US007001335B2

(12) United States Patent
Adachi et al.

(10) Patent No.: US 7,001,335 B2
(45) Date of Patent: Feb. 21, 2006

(54) ULTRASONIC WAVE GENERATING/TRANSMITTING APPARATUS

(75) Inventors: Kazunari Adachi, Yonezawa (JP); Tsuneyoshi Sugimoto, Machida (JP)

(73) Assignee: Aisin Kiko Co., Ltd., Aichi (JP)

( * ) Notice: Subject to any disclaimer, the term of this patent is extended or adjusted under 35 U.S.C. 154(b) by 0 days.

(21) Appl. No.: 10/451,125

(22) PCT Filed: Dec. 19, 2001

(86) PCT No.: PCT/JP01/11114

§ 371 (c)(1),
(2), (4) Date: Jan. 21, 2004

(87) PCT Pub. No.: WO02/49776

PCT Pub. Date: Jun. 27, 2002

(65) Prior Publication Data

US 2004/0133103 A1 Jul. 8, 2004

(30) Foreign Application Priority Data

Dec. 21, 2000 (JP) ............................ 2000-388742

(51) Int. Cl.
*A61B 8/00* (2006.01)

(52) U.S. Cl. ...................................... 600/437; 600/459

(58) Field of Classification Search ........ 600/437–472; 601/2–4

See application file for complete search history.

(56) References Cited

U.S. PATENT DOCUMENTS 4,867,141 A * 9/1989 Nakada et al. ................. 601/4
5,058,570 A * 10/1991 Idemoto et al. ................ 601/4
5,062,827 A 11/1991 Wiksell

FOREIGN PATENT DOCUMENTS

| | | |
|---|---|---|
| DE | 3940808 | 6/1991 |
| JP | 46-14879 | 5/1971 |
| JP | 62-152704 | 9/1987 |
| JP | 4-92211 | 8/1992 |
| JP | 5-46430 | 12/1993 |
| JP | 8-117243(A) | 5/1996 |
| JP | 9-36454 | 2/1997 |
| JP | 9-38099 | 2/1997 |
| JP | 2000-124519 | 4/2000 |

OTHER PUBLICATIONS

English Abstract for JP 8-117243(A) from European Patent Office esp@cenet database 12 Database.
English Abstract for JP 9-36454 from European Patent Office esp@cenet database 12 Database.
English Abstract for JP2000-124519 from European Patent Office esp@cenet database 12 Database.

* cited by examiner

*Primary Examiner*—Ali Imam
(74) *Attorney, Agent, or Firm*—MacMillan, Sobanski & Todd, LLC

(57) ABSTRACT

Disclosed is an ultrasonic generating and transmitting apparatus equipped with a transmission section for transmitting ultrasonic vibration from a vibration section. A plurality of linear members for transmitting ultrasonic vibration and binding plates which bind the linear members in such a state as to be apart from one another are provided. The transmission section is comprised of the linear members and the binding plates.

11 Claims, 3 Drawing Sheets

ULTRASONIC WAVE GENERATING/TRANSMITTING APPARATUS

CROSS REFERENCE TO RELATED APPLICATIONS

This application is a national phase of International Application No. PCT/JP01/11114 filed Dec. 19, 2001, the disclosures of which are incorporated herein by reference, and which claimed priority to Japanese Patent Application No. 2000-388742 filed Dec. 21, 2000, the disclosures of which are incorporated herein by reference.

BACKGROUND OF THE INVENTION

The present invention relates to an ultrasonic generating and transmitting apparatus suitable for use in destruction of calculi, such as a biliary calculus and renal calculus, destruction of cells such as of cancer or the like and ultrasonic cleaning or the like.

An ultrasonic generating and transmitting apparatus of this type is disclosed in Japanese Unexamined Utility Model Publication No. 62-152704 and Japanese Examined Utility Model Publication No. 5-46430. Ultrasonic vibration produced by an ultrasonic vibration section is transmitted via a transmission section which has a plurality of linear members bundled. A transmission section comprised of a single linear member has a small cross-sectional area and has such a shortcoming that it cannot transfer ultrasonic vibration sufficiently. The structure that binds a plurality of linear members together increases the cross-sectional area of the transmission section to be able to overcome the shortcoming.

Because each of the apparatuses in Japanese Laid-Open Utility Model Publication No. 62-152704 and Japanese Examined Utility Model Publication No. 5-46430 binds a plurality of linear members in such a way that adjoining linear members contact each other, however, the adjoining linear members rub each other, thus generating heat. Therefore, a cooling device for preventing heat generation as disclosed in Japanese Laid-Open Utility Model Publication No. 62-152704 becomes essential, thus enlarging the ultrasonic generating and transmitting apparatus. The enlargement of an ultrasonic generating and transmitting apparatus is particularly inconvenient in an ultrasonic treatment device or the like which is used by inserting it in a human body.

The present invention aims at providing an ultrasonic generating and transmitting apparatus which can suppress heat generation even in the case where a transmission section is constituted by binding a plurality of linear members.

BRIEF SUMMARY OF THE INVENTION

The present invention is directed to an ultrasonic generating and transmitting apparatus equipped with a transmission section for transmitting ultrasonic vibration from a vibration section. According to a preferable embodiment of the present invention, there are provided a plurality of linear members for transmitting ultrasonic vibration, and binding means for binding the linear members in such a state as to be apart from one another, and the transmission section is comprised of those linear members and binding means. As the plural linear members bound are separated from one another, heat generation between adjoining linear members which are transmitting ultrasonic vibration is avoided.

According to another embodiment of the present invention, an ultrasonic generating and transmitting apparatus is equipped with a vibration section for generating ultrasonic, an insert tube coupled to the vibration section and an operational section which is located at a distal end of the insert tube and to which ultrasonic vibration is transmitted. The insert tube has a plurality of linear members, a plurality of binding plates for binding the plurality of linear members and a protection cover for covering around the plurality of linear members and the plurality of binding plates. Even such an embodiment affords operational advantages similar to those of the aforementioned embodiment. Further, the protection cover prevents the vibration portions of the other linear members than the distal end portions from contacting something other than the ultrasonic generating and transmitting apparatus.

DETAILED DESCRIPTION OF THE PREFERRED EMBODIMENTS

Figure 1:
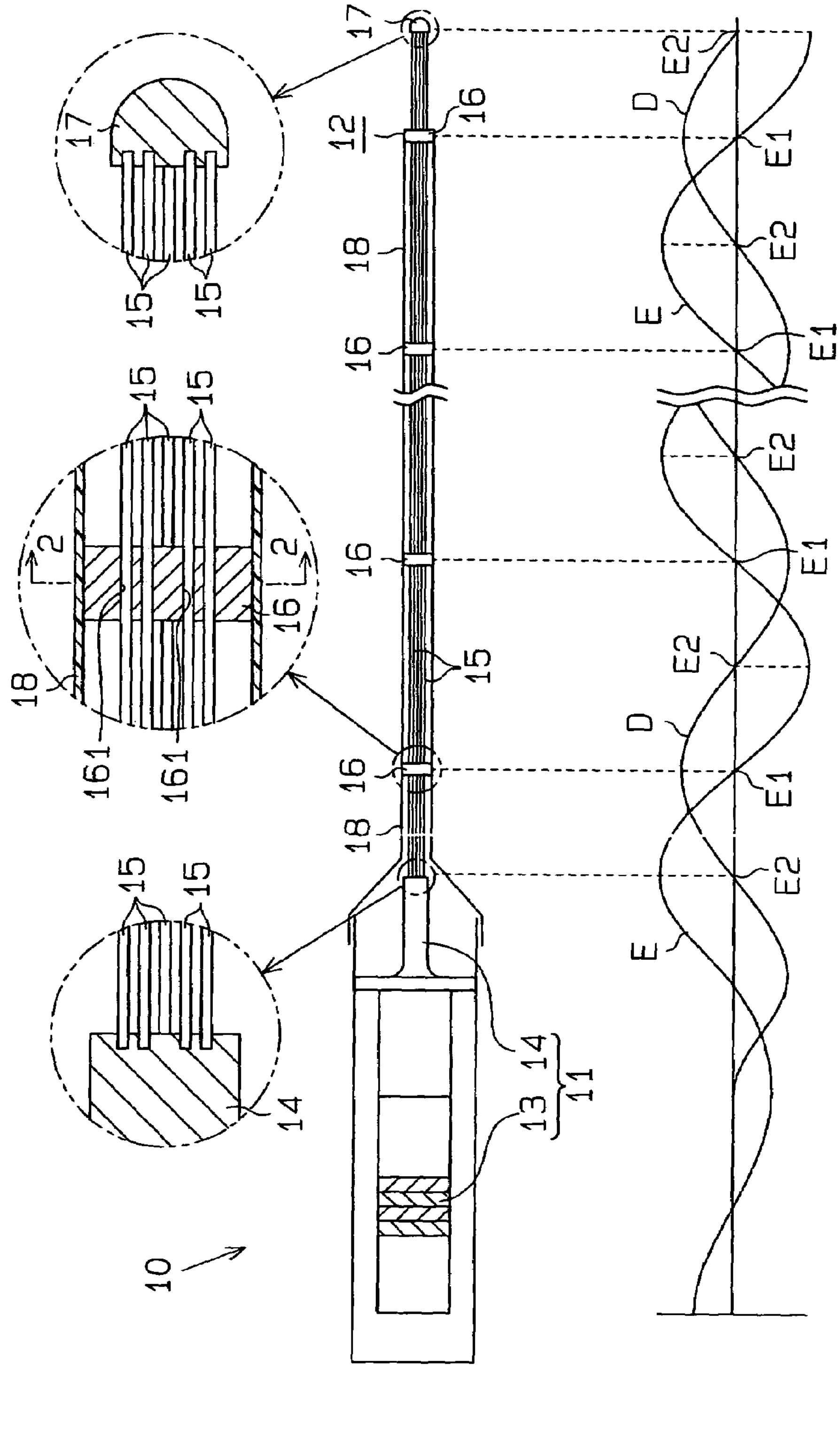
FIG. 1 is a side cross-sectional view with an enlarged cross-sectional view of essential portions and a graph incorporated, showing a first embodiment of an ultrasonic generating and transmitting apparatus.
Figure 2:
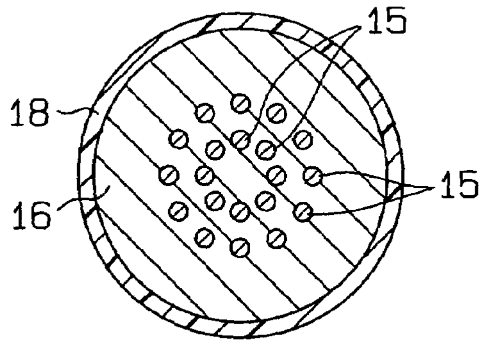
FIG. 2 is a cross-sectional view taken along the line 2—2 in FIG. 1.

A first embodiment of an ultrasonic generating and transmitting apparatus embodying the present invention will be described below based on FIGS. 1 to 3. FIG. 1 shows an ultrasonic generating and transmitting apparatus 10 with a structure suitable for an ultrasonic treatment device. The ultrasonic generating and transmitting apparatus 10 comprises a vibration section 11 which generates ultrasonic and an insert tube 12 coupled to the vibration section 11.

The vibration section 11 has a vibrator 13 which oscillates with the supply of an electric signal, and a conical horn 14 linked to the vibrator 13. A Langevin vibrator, for example, is used in the vibration section 11. The horn 14 amplifies ultrasonic vibration produced by the vibrator 13.

The insert tube 12 comprises a plurality of linear members 15 with a single core shape, a plurality of disk-like binding plates 16 which bind the plural linear members 15, an operational section 17 coupled to the distal end portions of the plural linear members 15, and a protection cover 18 which covers around the plural linear members 15 and the plural binding plates 16. The linear members 15 with a circular cross section transmit ultrasonic vibration, amplified by the horn 14, to the operational section 17. The operational section 17, to which the ultrasonic vibration has been transmitted via the plural linear members 15, is used for incision and lithotripsy of an affected part in contact with it.

The linear members 15 are made of a material which has a good ultrasonic vibration transmission efficiency and is easily bendable. A suitable material for the linear members 15 is, for example, stainless steel, titanium alloy or elastic alloy or the like. A material for the binding plates 16 is a light and very strong material, for example, a magnesium metal or a metal essentially consisting of magnesium. Hereinafter, those metals are called magnesium-based metals. The protection cover 18 is formed of an easily bendable elastic material, for example, a synthetic resin.

Figure 3:
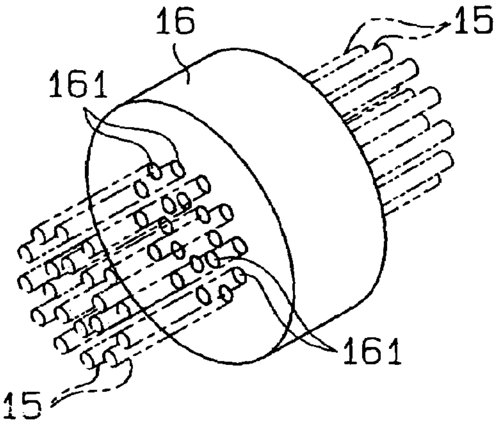
FIG. 3 is a perspective view of a binding plate.

As shown in FIG. 3, a plurality of support holes 161 which penetrate through the binding plate 16 are formed in the binding plate 16 in such a way as to be separated from one another. The individual support holes 161 with a circular cross section are laid out on a pair of concentric circles (not shown) that have the same center as the center of the disk-like binding plate 16. The individual support holes 161 are laid out on the respective circles at equidistances. As shown in FIG. 2, the linear members 15 are merely inserted into the respective support holes 161 without being secured there. In the illustrated example, a support hole is not provided in the centers of the circles, nor is a linear member 15 inserted there, but a linear member 15 may be inserted in a support hole which may be provided in the centers of the circles.

The proximal end portions of the individual linear members 15 are coupled, by welding, to the distal end portion of the horn 14 where the stress is the smallest. That is, the middle portions of the plural linear members 15 are bound by the binding plates 16 in such a way as to be separated from one another, and both ends of the plural linear members 15 are bound by the horn 14 and the operational section 17 in such a way as to be separated from each other.

A curve E shown in FIG. 1 represents the distribution curve of the ultrasonic vibration amplitude caused by the oscillation of the vibrator 13, and a curve D represents the distribution curve of stress. A point E1 in the curve E is the position of a vibratory node (a portion where the curve crosses the horizontal line) of the ultrasonic vibration amplitude and a point E2 in the curve E is the position of a vibratory loop (a portion where the vertical line from the peak or trough of the curve crosses the horizontal axis) of the ultrasonic vibration amplitude. The coupled portion of the horn 14 and the linear members 15 is so set as to correspond to the vibratory loop E2 of the ultrasonic vibration amplitude and the coupled portion of the operational section 17 and the linear members 15 is so set as to correspond to the vibratory loop E2 of the ultrasonic vibration amplitude. That is, when the vibrator 13 oscillates, a standing wave indicated by a curve E is generated in the linear members 15.

The binding plate 16 binds the plural linear members 15 at the position of the vibratory node E1 of the ultrasonic vibration amplitude. The thickness center of the binding plate 16 coincides with the position of the vibratory node E1 of the ultrasonic vibration amplitude. In the embodiment, the binding plates 16 are laid out at the positions of all the vibratory nodes E1 of the ultrasonic vibration amplitude in the lengthwise range of the linear members 15. The protection cover 18 is coupled to the surfaces of the binding plates 16 that bind the plural linear members 15, apart from one another, at the vibratory nodes E1, so that the protection cover 18 does not contact the linear members 15 even in the case where the insert tube 12 is bent.

The first embodiment has the following advantages.

(1—1) The plural linear members 15 bound by the binding plates 16 or binding means are separated from one another. Therefore, the linear members 15 which transmit ultrasonic vibration do not rub against one another, so that heat originated from rubbing of the linear members 15 is not generated. Such avoidance of heat generation eliminates the need for cooling means for cooling the insert tube 12 that becomes a transmission section for transmitting ultrasonic vibration from the vibration section 11. Therefore, the problem that the use of the cooling means enlarges the ultrasonic generating and transmitting apparatus is overcome.

(1-2) The linear members 15 do not vibrate at the vibratory node E1 of the ultrasonic vibration amplitude. Therefore, rubbing hardly occurs between the binding plate 16 that binds the linear members 15, without fixing them, at the vibratory node E1 of the ultrasonic vibration amplitude and the linear members 15. Therefore, heat generation caused by rubbing between the binding plate 16 and the linear members 15 is suppressed.

(1-3) In the case where a plurality of linear members 15 are bound at the vibratory loop E2 of the ultrasonic vibration amplitude as in the apparatus of Japanese Examined Utility Model Publication No. 5-46430, the cross-sectional area at the binding portion or the vibratory loop that vibrates increases, making it complex to compute the proper cross-sectional area at this binding portion (calculation of a boundary condition). Such complication of calculation makes the design of the apparatus hard. In the embodiment in which the plural linear members 15 are-bound at the vibratory node E1 of the ultrasonic vibration amplitude where there is no vibration of the ultrasonic vibration amplitude, it is unnecessary to calculate the cross-sectional area of the binding plate 16 (the area of the cross section shown in FIG. 2) as the boundary condition in the aforementioned sense. The design of the apparatus therefore becomes simpler as compared with the apparatus of Japanese Examined Utility Model Publication No. 5-46430.

(1-4) Because the layout position of the binding plate 16 as contact inhibition means corresponds to the vibratory node E1 of the ultrasonic vibration amplitude, the vibration of the linear members 15 is not transmitted to the protection cover 18. Therefore, the protection cover 18 can achieve its intended role of preventing the vibration portions of other portions of the linear members 15.than the distal end portions from contacting anything other than the ultrasonic generating and transmitting apparatus 10.

(1-5) In the case where an affected portion is incised or subjected to lithotripsy using the apparatus of Japanese Examined Utility Model Publication No. 5-46430, the insert tube may be bent to reach the affected part. In the case where the apparatus of Japanese Utility Model Publication No. Hei 5-46430 is bent, however, the binding portion that binds a plurality of linear members is likely to contact the protection cover. As the binding portion is at the position of the vibratory loop of the ultrasonic vibration amplitude, there arises a problem such that the protection cover that is in contact with the binding portion is worn out or is melted by heat.

In the present embodiment, the protection cover 18 is supported in such a way as to be apart from any linear member 15 by the binding plates 16 laid out in association with all the vibratory nodes E1 of the ultrasonic vibration amplitude in the lengthwise range of the linear members 15. That is, every vibratory loop E2 of the ultrasonic vibration amplitude in the lengthwise range of the linear members 15, excluding both end portions of the linear members 15, is positioned between adjoining binding plates 16. Even in the case where the insert tube 12 is bent, therefore, it becomes less likely that the vibratory loop E2 of the ultrasonic vibration amplitude contacts the protection cover 18. That is, as the protection cover 18 is supported in such a way as to be apart from the linear members 15 by the binding plates 16 laid out at the vibratory nodes E1 of the ultrasonic vibration amplitude, it is possible to increase the bending allowance of the insert tube 12 in the range where the linear members 15 do not contact the protection cover 18.

(1-6) It is easy to form the binding plate 16 having the support holes 161 for insertion of the linear members 15. The binding plate 16 which permits the plural linear members 15 to be inserted apart from one another is simple as binding means that binds the plural linear members 15 in such a way as to be apart from one another.

(1-7) The ultrasonic generating and transmitting apparatus with a structure suitable for an ultrasonic treatment device requires to be lighter from the viewpoint of the operability. A magnesium-based metal which is light and very strong is suitable as the material for the binding plates 16.

Figure 4:
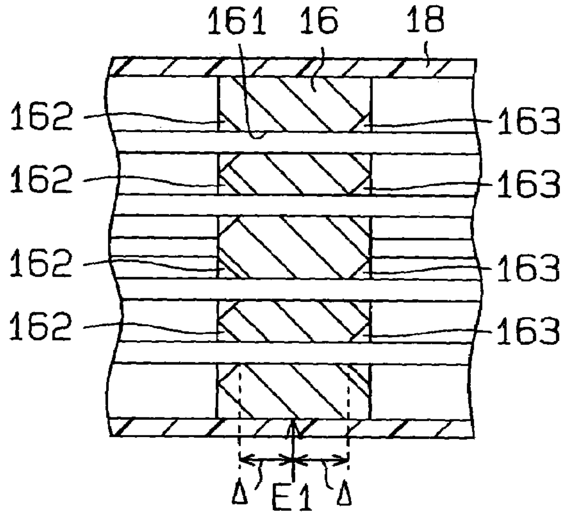
FIG. 4 is an enlarged cross-sectional view of essential portions showing a second embodiment of an ultrasonic generating and transmitting apparatus.

A second embodiment of the present invention will now be discussed referring to FIG. 4. Same symbols are used for the same structural portions as those of the first embodiment.

Funnel-like tapers 162 and 163 are provided at each opening of the support hole 161 of the binding plate 16. Given that the thickness of the binding plate 16 is the same as that of the first embodiment, therefore, the contact range of the binding plate 16 with respect to the linear members 15 becomes shorter than that of the first embodiment. In this embodiment, the thickness center of the binding plate 16 is made to coincide with the position of the vibratory node E1 of the ultrasonic vibration amplitude. Therefore, the length Δ (shown in FIG. 4) by which the contact portion of the linear member 15 and the binding plate 16 is deviated most from the position of the vibratory node E1 of the ultrasonic vibration amplitude becomes shorter than that of the first embodiment. The degree of friction between the linear members 15 which are vibrating and the binding plate 16 becomes larger, increasing the possible occurrence of heat generation and wear-out, as the deviation length Δ becomes greater. Therefore, the shorter the deviation length Δ is, the better it is, and the tapers 162 and 163 are simple means to shorten the deviation length Δ.

Figure 5:
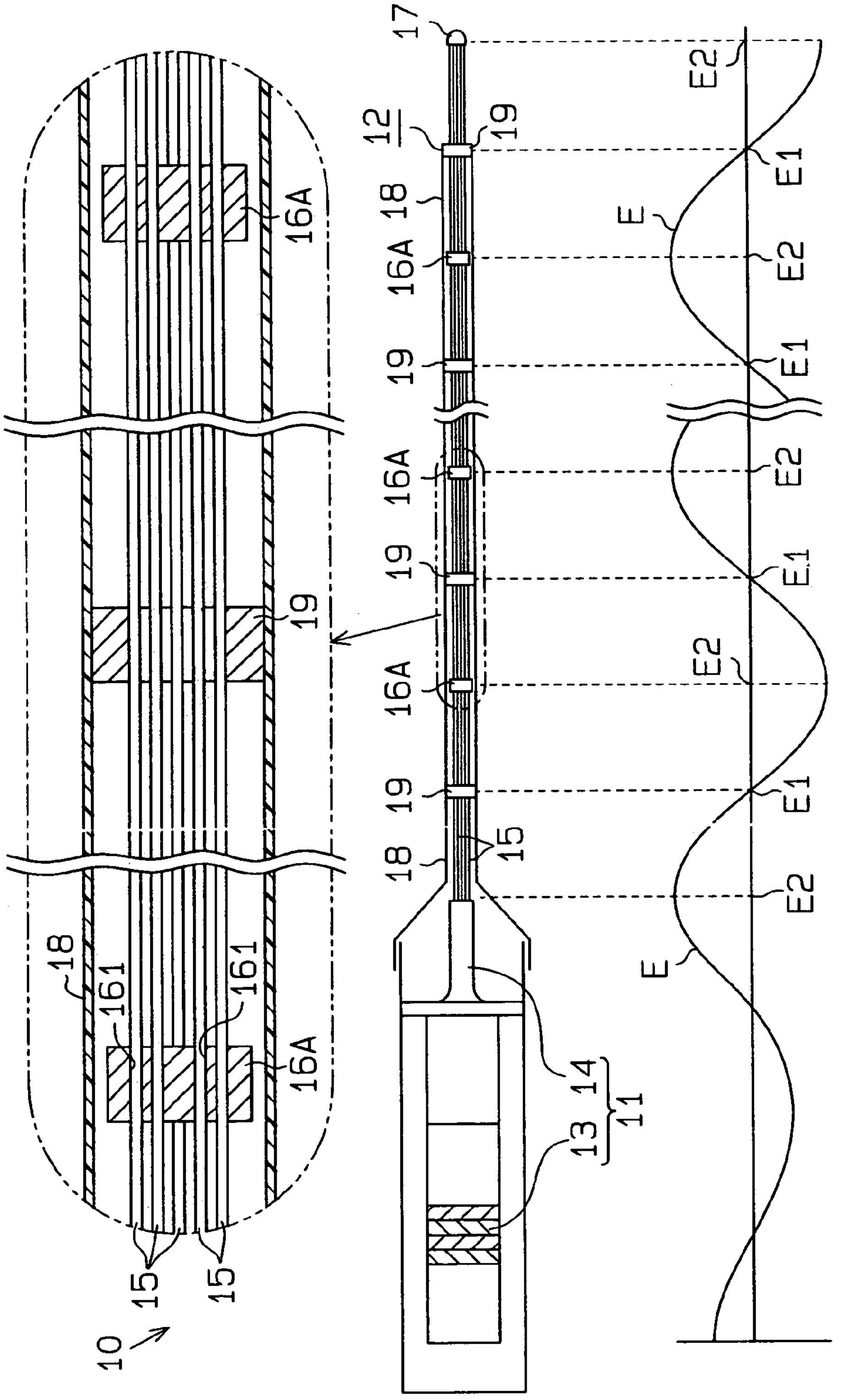
FIG. 5 is a side cross-sectional view with an enlarged cross-sectional view of essential portions and a graph incorporated, showing a third embodiment of an ultrasonic generating and transmitting apparatus.

A third embodiment of the present invention shown in FIG. 5 will be discussed next. Same symbols are used for the same structural portions as those of the first embodiment.

A binding plate 16A of a magnesium-based metal in this embodiment is laid out in association with the vibratory loop E2 of the ultrasonic vibration amplitude. The linear members 15 and the binding plate 16A are secured in the support holes 161 by welding. The protection cover 18 is coupled to the outer surface of a support ring 19 of a magnesium-based metal placed at the position of the vibratory node E1 of the ultrasonic vibration amplitude. All the linear members 15 are inserted inside the support ring 19. The binding plate 16A or binding means is separated from the protection cover 18.

The third embodiment affords the same advantages as those in (1—1), (1-6) and (1-7) of the first embodiment. The support ring 19 serves to prevent the contact between the linear members 15 and the protection cover 18. Although the inner surface of the support ring 19 which is contact inhibition means contacts some linear members 15, the layout position of the support ring 19 corresponds to the vibratory node E1 of the ultrasonic vibration amplitude so that the vibration of the linear members 15 is not transmitted to the protection cover 18. Therefore, the support ring 19 brings about the same advantage as that in (1-4) of the first embodiment. Further, the support ring 19 increases the bending allowance of the insert tube 12 in the range where the linear members 15 do not contact the protection cover 18.

The present invention may also take the following modes.

(1) The binding plate 16 is fixed to the linear members 15 by welding or the like.

(2) The binding plate 16 is laid out at a position slightly shifted from the position of the vibratory node E1 of the ultrasonic vibration amplitude.

(3) The binding plates 16 are intermittently laid out with respect to the positions of the vibratory nodes E1 of the ultrasonic vibration amplitude in the lengthwise range of the linear members 15. That is, in the case where the protection cover 18 can be made not to contact the linear members 15 while coping with the demanded easy bending of the insert tube 12, the binding plates 16 need not be placed at the positions of all the vibratory nodes E1 of the ultrasonic vibration amplitude in the lengthwise range of the linear members 15.

(4) The tapers 162 and 163 in the second embodiment may cross each other so that the binding plate 16 has a line contact with the linear members 15.

(5) The binding plates 16, 16A are formed of the same material as that of the linear members 15.

What is claimed is:

1. An ultrasonic generating and transmitting apparatus comprising a vibration section and a transmission section for transmitting ultrasonic vibrations from said vibration section, wherein said transmission section comprises:

a plurality of linear members for transmitting ultrasonic vibration; and binding means for binding said linear members individually, so as to be apart from one another, wherein said binding means is comprised of a plurality of binding plates and said linear members are inserted into the binding plates, wherein said ultrasonic vibration has an amplitude having vibratory nodes, wherein said each binding plate binds said linear members near each of said vibratory nodes.

2. The ultrasonic generating and transmitting apparatus according to claim 1, wherein a protection cover covers said linear members and wherein a contact inhibition means for setting said linear members apart from said protection cover is intervened between said linear members and said protection cover.

3. The ultrasonic generating and transmitting apparatus according to claim 2, wherein said contact inhibition means serves as said binding means and said protection cover is supported by said binding means in such a way as to he separated from said linear members.

4. The ultrasonic generating and transmitting apparatus according to claim 1, wherein said linear member are inserted into the binding plates without being secured to said binding plates.

5. The ultrasonic generating and transmitting apparatus according to claim 1, wherein said linear members are secured into the binding plates.

6. The ultrasonic generating and transmitting apparatus according to claim 1, wherein said binding plates are made of a magnesium-based metal.

7. An ultrasonic generating and transmitting apparatus equipped with a vibration section for generating an ultrasonic vibration, an insert tube coupled to the vibration section, and an operational section which is located at a distal end of the insert tube and to which said ultrasonic vibration is transmitted, said insert tube comprising a plurality of linear members, a plurality of binding plates for binding the plurality of linear members, and a protection cover for covering the plurality of linear members and the plurality of binding plates, wherein said ultrasonic vibration has an amplitude having vibratory node portions, and said binding plates bind said linear members near said vibratory node portions.

8. The ultrasonic generating and transmitting apparatus according to claim 7, wherein said linear members have a circular cross section.

9. The ultrasonic generating and transmitting apparatus according to claim 7, wherein said vibration section has a vibrator, which oscillates with supply of an electric signal to generate said ultrasonic vibrations, and a horn coupled to that vibrator, and said horn amplifies said ultrasonic vibrations produced by said vibrator.

10. The ultrasonic generating and transmitting apparatus according to claim 9, wherein said linear members transmit the ultrasonic vibrations amplified by said horn to said operational section.

11. The ultrasonic generating and transmitting apparatus according to claim 9, wherein said ultrasonic vibration has an amplitude having vibratory nodes, wherein said binding plates bind said linear members near said vibratory nodes.

* * * * *

UNITED STATES PATENT AND TRADEMARK OFFICE
CERTIFICATE OF CORRECTION

PATENT NO. : 7,001,335 B2 — Page 1 of 1
DATED : February 21, 2006
INVENTOR(S) : Kazunari Adachi and Tsuneyoshi Sugimoto It is certified that error appears in the above-identified patent and that said Letters Patent is hereby corrected as shown below:

Title page,
Item [54], Title, "ULTRASONIC WAVE GENERATING/TRANSMITTING APPARATUS" should read -- ULTRASONIC GENERATING AND TRANSMITTING APPARATUS --.

Signed and Sealed this

Ninth Day of May, 2006

JON W. DUDAS
*Director of the United States Patent and Trademark Office*